US008082917B2

(12) United States Patent
Ooida

(10) Patent No.: US 8,082,917 B2
(45) Date of Patent: Dec. 27, 2011

(54) INHALER

(75) Inventor: Junichi Ooida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 631 days.

(21) Appl. No.: 12/256,518

(22) Filed: Oct. 23, 2008

(65) Prior Publication Data

US 2009/0107492 A1 Apr. 30, 2009

(30) Foreign Application Priority Data

Oct. 30, 2007 (JP) ................................. 2007-281145

(51) Int. Cl.
*A61M 11/00* (2006.01)

(52) U.S. Cl. .............................. 128/200.14; 128/200.21

(58) Field of Classification Search ............. 128/200.22, 128/200.21, 200.14, 200.23, 200.24, 203.12, 128/203.14, 203.15, 203.23, 203.24, 200.16, 128/204.21; 222/52, 54, 310
See application file for complete search history.

(56) References Cited

U.S. PATENT DOCUMENTS 6,923,179 B2 * 8/2005 Gupta et al. ............. 128/203.17
2001/0020448 A1 * 9/2001 Vaartstra et al. .............. 118/724
2008/0066749 A1 * 3/2008 Reichert et al. .......... 128/203.12
2008/0092880 A1 4/2008 Ooida et al. ............. 128/200.14
2008/0092888 A1 * 4/2008 Haroutunian ............ 128/203.29
2008/0216824 A1 9/2008 Ooida ...................... 128/200.21

FOREIGN PATENT DOCUMENTS

WO WO 95/01137 12/1995
WO WO 96/09846 4/1996
WO WO 00/24362 4/2000
WO WO 02/04043 1/2002

* cited by examiner

*Primary Examiner* — Justine Yu
*Assistant Examiner* — Colin W Stuart
(74) *Attorney, Agent, or Firm* — Fitzpatrick, Cella, Harper & Scinto

(57) ABSTRACT

There is provided an inhaler that allows inhalation of droplets having a fixed diameter, regardless of the use condition of the inhaler. The inhaler allows a user to inhale medicine from a suction port thereof. The inhaler includes an air passage through which the medicine passes, the air passage being connected to the suction port, an opening attached to a medicine ejection portion for ejecting the medicine, and provided in a part of the air passage so that the ejected medicine is released into the air passage therethrough, a passage-length determining portion configured to determine the proper distance from the opening to the suction port in accordance with a size of droplets of the medicine ejected from the medicine ejection portion and/or an ejection frequency, and a passage-length changing mechanism configured to change the distance from the opening to the suction port.

6 Claims, 9 Drawing Sheets

FIG. 8

| | | $\phi$ 0 [$\mu$m] | | | | |
|---|---|---|---|---|---|---|
| | | 3.5 | 4.0 | 4.5 | 5.0 | 5.5 |
| f [KHz] | 20 | 2.66 | 6.06 | 10.20 | 15.02 | 20.65 |
| | 40 | 2.72 | 6.26 | 10.73 | 16.28 | 23.51 |
| | 60 | 2.79 | 6.49 | 11.35 | 17.88 | 27.21 |
| | 80 | 2.85 | 6.72 | 12.05 | 19.84 | 32.31 |
| | 100 | 2.91 | 6.96 | 12.86 | 22.18 | 40.03 |

* UNIT OF DISTANCE: cm

INHALER

BACKGROUND OF THE INVENTION

1. Field of the Invention

The present invention relates to an inhaler for ejecting medicine, aromas, nicotine, etc., in the form of droplets so that the user can inhale the droplets.

2. Description of the Related Art

With recent advances in medicine and science, the average life expectancy has increased and society is becoming more elderly as a whole. On the other hand, however, new diseases and infections due to changes in dietary life and living environments, environmental pollution, and viruses and fungi have been found. This increases people's anxiety about health. In particular, in countries referred to as developed countries, it is important to cope with increases in the number of patients with lifestyle diseases, such as diabetes and hypertension, and to improve cures for such diseases.

For example, since insulin is not secreted in diabetics, particularly, Type I insulin-dependent diabetics, it is necessary for diabetics periodically to inject themselves with insulin. While insulin is currently injected by hypodermic injection, this imposes heavy physical and mental burdens on the diabetics. In order to reduce the burdens on the patient, a pen-shaped syringe that has a thin needle so as to cause little pain to the patient has been developed. However, Type I diabetics frequently live lifestyles similar to those of healthy persons except for the necessary periodical insulin injections. Therefore, even when the syringe is pen-shaped, the diabetic patient may be mentally hesitant to take an insulin shot in public, and therefore, it may be difficult to take insulin shots at appropriate times. As a result, this method may hinder proper procedures for diabetic sufferers.

As another solution, a method in which the user inhales medicine with an inhaler has been developed. In this method for administering medicine through the respiratory system, the user does not feel any pain, unlike when using a syringe. For example, International Publications Nos. WO95/01137 and WO02/04043 disclose inhalers in which the principle of an inkjet method is applied to ejection.

When such inhalers are used, it is necessary accurately to manage the dosage and dose interval of medicine according to the relevant prescriptions, and efficiently to apply the medicine under proper ejection control. For example, the diameter of droplets of medicine at a suction port (the portion to be held in the user's mouth to inhale the medicine) of an inhaler has an influence on the probability that the medicine will reach the alveoli. For this reason, it is preferable that the inhaler provide droplets having a fixed diameter, regardless of the use condition thereof. Unfortunately, the user does not always use the same ejection unit, according to the phase of treatment. While the diameter and ejection frequency of medicine droplets to be ejected have an effect on the amount of moisture evaporation from the droplets during their flight from the inhaler into the patient's body, they may vary according to the ejection unit being used. In other words, even when the inhaler is used in the same environment every time, the diameter of droplets at the suction port may change according to the use condition of the inhaler. This hinders consistent inhalation of the proper dosage prescribed by the doctor. International Publication No. WO1996/009846 discloses an inhaler in which evaporation is promoted with a heater and a dehumidifier so as to obtain droplets having a fixed diameter. As another method for promoting evaporation, International Publication No. WO00/24362 discloses an inhaler in which a passage of a mouthpiece is extended.

Type I diabetics who rely on inhalers must always carry the inhalers, because of the necessity for the periodic administration of medicine. Therefore, there is a demand for a small and lightweight inhaler that allows a user to inhale droplets having a fixed diameter, regardless of the use condition.

However, in the inhaler described in International Publication No. WO1996/009846, a heater and a dehumidifier are necessary as generating devices that generate gas for promoting evaporation. When all the energy necessary for driving the inhaler is to be provided from a source in the inhaler, in consideration of portability, the need to sufficient an energy to drive the generating devices can result in a structure that increases the size and weight of the inhaler.

International Publication No. WO00/24362 does not specify a variable that serves as a basis of control of the length of the passage in the mouthpiece. As a result of this, also, the size and weight of the inhaler may be increased.

SUMMARY OF THE INVENTION

The present invention provides a small and lightweight inhaler that allows medicine to be inhaled in the form of droplets having a fixed diameter, regardless of the use condition of the inhaler.

An inhaler according to an aspect of the present invention allows a user to inhale medicine from a suction port thereof. The inhaler includes an air passage through which the medicine passes, the air passage being connected to the suction port; an opening attached to a medicine ejection portion for ejecting the medicine, and provided in a part of the air passage so that the ejected medicine is released into the air passage therethrough; a passage-length determining portion configured to determine a distance from the opening to the suction port in accordance with a size of droplets of the medicine ejected from the medicine ejection portion and/or an ejection frequency; and a passage-length changing mechanism configured to change the distance from the opening to the suction port.

With the above-described configuration, the inhaler provides the following advantages.

By changing the distance from the opening to the suction port in the air passage in accordance with the use condition of the inhaler, the flying time of the ejected droplets can be changed. By virtue of this it has proved to be possible to provide droplets having a fixed diameter to be inhaled, regardless of the use condition of the inhaler.

The user can adjust the length of the air passage. In this case, since the inhaler does not consume any energy in the process of controlling the droplet diameter, the size and weight of the inhaler can be reduced.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 8 is a table showing the relationship among the change amount of the passage length, the size of ejected droplets, and the ejection frequency.

DETAILED DESCRIPTION OF THE PREFERRED EMBODIMENTS

The preferred embodiments of the present invention will now be described in detail in accordance with the accompanying drawings.

First Embodiment

Figure 1:
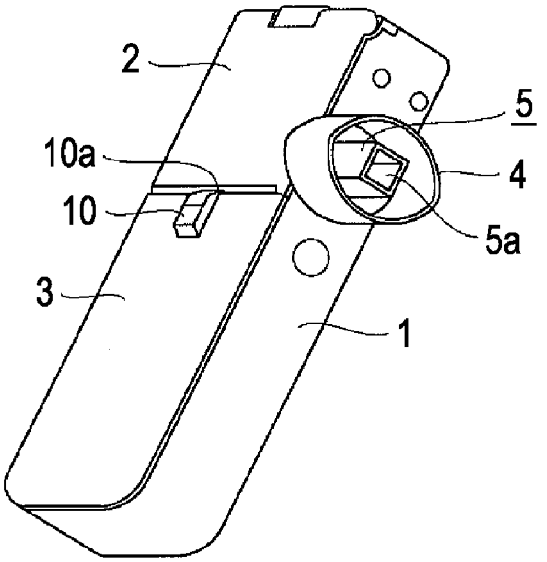
FIG. 1 is a schematic perspective view of an inhaler according to a first embodiment.

FIG. 1 is an external perspective view of an inhaler according to a first embodiment.

Referring to FIG. 1, an access cover 2 and a front cover 3 are provided on one surface of a box-shaped housing body 1. The front cover 3 is provided as an integral part of the housing body 1 and serves as one portion of that surface of the housing body 1, at one end of the housing body 1. The access cover 2 is pivotally attached via a hinge 2*a* to an edge on the other end of the housing body 1 in the longitudinal direction. The access cover 2 is always biased in an opening direction by a return spring (not shown). In order to prevent the access cover 2 from being opened when not desired, the front cover 3 is provided with a lock lever 10 having a projection 10*a* to be engaged with a leading end (free end) of the access cover 2.

When the lock lever 10 is slid against the elastic force of the return spring, the projection 10*a* disengages from the leading end of the access cover 2, and the access cover 2 pivots open on a hinge shaft (not shown) under the elastic force of the return spring.

Figure 2:
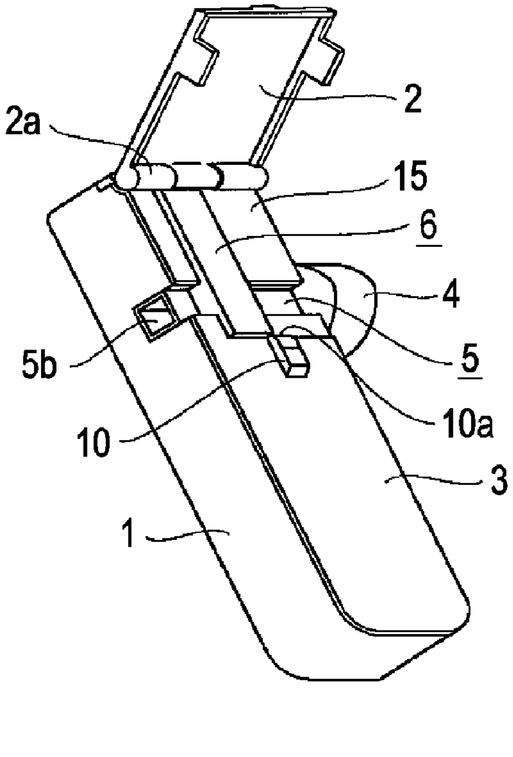
FIG. 2 is a schematic perspective view showing a state in which an access cover of the inhaler shown in FIG. 1 is open.

When the access cover 2 is opened, as shown in FIG. 2, a medicine cartridge 6 (shown by itself in FIG. 3) appears. The medicine cartridge 6 is a combination of an ejection head 8 serving as a medicine ejection portion for ejecting medicine and a reservoir 7 for storing the medicine. The medicine cartridge 6 and a mouthpiece 4 are removably supported in a guide portion 15 of the housing body 1.

An air passage (air flow path) 5 is connected to a suction port 5*a* provided in the mouthpiece 4. Medicine ejected from the ejection head 8 passes through the air passage 5, and is then guided to the suction port 5*a*. When the user performs an inhalation operation, air enters through an air inlet 5*b* and an air flow is produced in the air passage 5. The ejected medicine is carried by the air flow.

Figure 3:
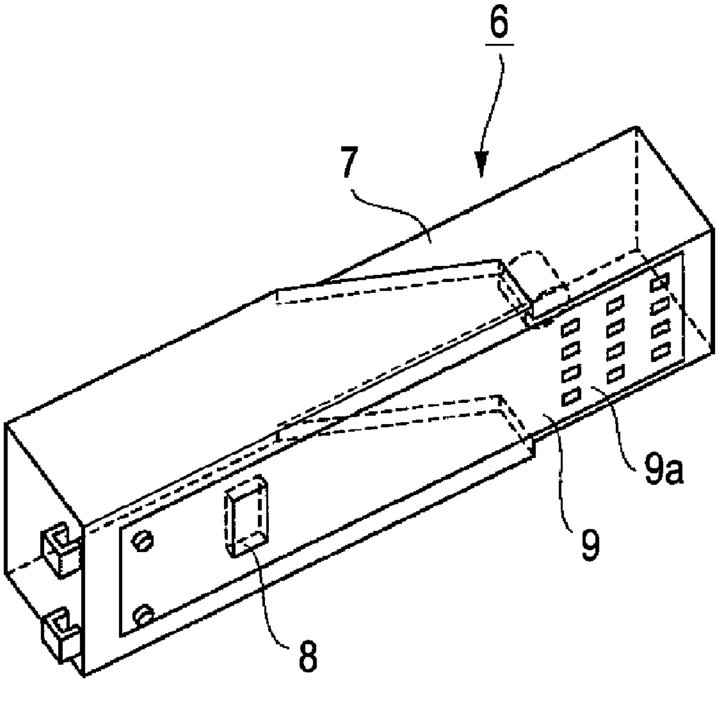
FIG. 3 is a schematic perspective view of a medicine cartridge in the inhaler shown in FIG. 1.

FIG. 3 is a schematic perspective view of the medicine cartridge 6. The medicine cartridge 6 includes the reservoir 7 for storing medicine, the ejection head 8 for ejecting the medicine supplied from the reservoir 7 in the form of droplets, and a wiring board 9 having an electrical connection surface 9*a* that is to be in contact with a battery 18 (see FIG. 12) for supplying power to ejection-energy generating elements provided in the ejection head 8. As the battery 18, a rechargeable secondary cell is used.

While the medicine can be ejected by an arbitrary method, it is preferably ejected by applying heat energy with an electrothermal transducer (thermal inkjet method) or applying mechanical energy with an electromechanical transducer such as a piezoelectric element (piezoelectric inkjet method). Particularly, the thermal inkjet method is used preferably.

The use of the thermal inkjet method can increase the bore of ejection ports, the amount of heat of heating pulses used for ejection, the size accuracy of a microheater for heating, and reproducibility in the medicine cartridge. For this reason, it is possible to obtain a narrow droplet diameter distribution. Moreover, the head manufacturing cost is low, and applicability to small apparatuses in which frequent replacement of the head is necessary is high. Therefore, particularly when the apparatus is required to have high portability and convenience, it is preferable that the ejection device use the thermal inkjet method.

In the present invention, the ejection head 8 can be combined with the reservoir 7 to form the medicine cartridge 6, as shown in the drawings, or can be provided separately from the reservoir 7.

Figure 4:
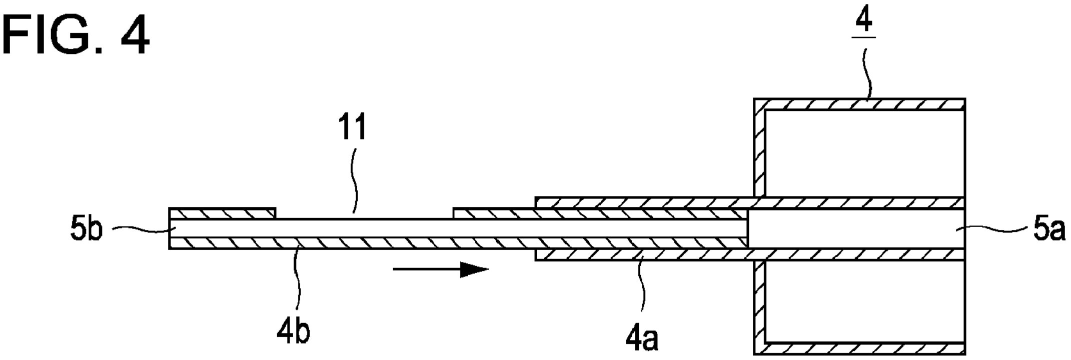
FIG. 4 is a schematic cross-sectional view of a passage-length changing unit in the inhaler according to the first embodiment.

FIG. 4 explains a passage-length changing mechanism provided in the inhaler according to the first embodiment, and shows a cross-section of the mouthpiece 4. The air passage 5 includes a first passage forming member 4*a* having the suction port 5*a*, and a second passage forming member 4*b* that is fitted in the first passage forming member 4*a* so as to slide in the axial direction. This slide mechanism serves as a passage-length changing mechanism. The first passage forming member 4*a* is a shaft member connected to the mouthpiece 4, and holds the second passage forming member 4*b* so that the second passage forming member 4*b* can slide. The first passage forming member 4*a* and the second passage forming member 4*b* are combined to form the air passage 5. The second passage forming member 4*b* has an opening 11 through which medicine ejected from the ejection head 8 of the medicine cartridge 6 is released into the air passage 5. By relatively sliding the first passage forming member 4*a* and the second passage forming member 4*b* in the axial direction, the distance from the opening 11 to the suction port 5*a* can be changed. Hereinafter, the distance from the opening 11 to the suction port 5*a* is sometimes referred to as the "passage length".

Figure 5:
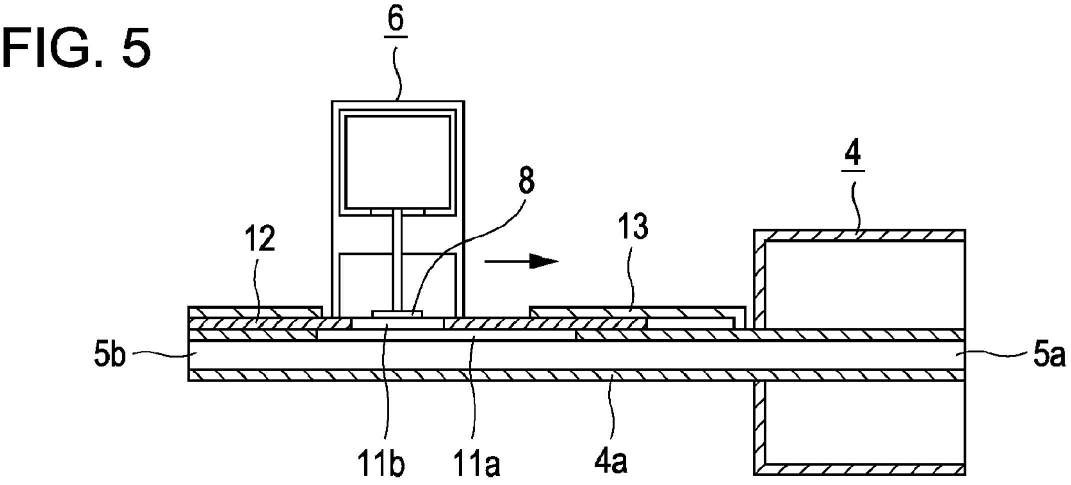
FIG. 5 is a schematic cross-sectional view of a modification of a passage-length changing unit.

FIG. 5 is a schematic cross-sectional view showing a modification of a passage-length changing mechanism. This passage-length changing mechanism includes only a passage forming member 4*a* serving as a shaft member of a mouthpiece 4 to be held in the user's mouth. A boundary plate 12 covers a communication hole 11 provided in the passage forming member 4*a* from the outside. The boundary plate 12 can slide in the axial direction along a slide-direction guide plate 13. The boundary plate 12 has an opening 11*b* through which droplets ejected from the ejection head 8 are guided into an air flow in the air passage. By moving the boundary plate 12 in the direction of the arrow in FIG. 5 or in the direction opposite thereto, the distance between the opening 11*b* and a suction port 5*a* can be changed.

Figure 6:
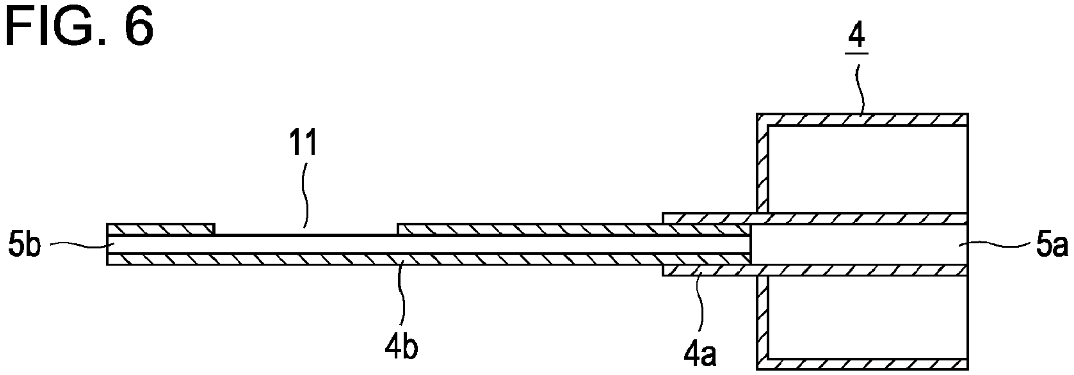
FIG. 6 is a schematic cross-sectional view of another modification of a passage-length changing unit.

FIG. 6 is a schematic cross-sectional view showing another modification of a passage-length changing mechanism. In this passage-length changing mechanism, the distance from an opening 11 to a suction port 5*a* can be changed by replacing a first passage forming member 4*a*, which serves as a shaft member of a mouthpiece 4, with another passage forming member having a different length. The first passage forming member 4*a* and a second passage forming member 4*b* are threaded so as to be removably connected to each other. Therefore, it is possible to connect a mouthpiece 4 in which a shaft member has a length set in accordance with the use environment of the inhaler. Consequently, it is possible to change the passage length of the air passage, that is, the distance from the opening 11 to the suction port 5*a*.

Figure 7:
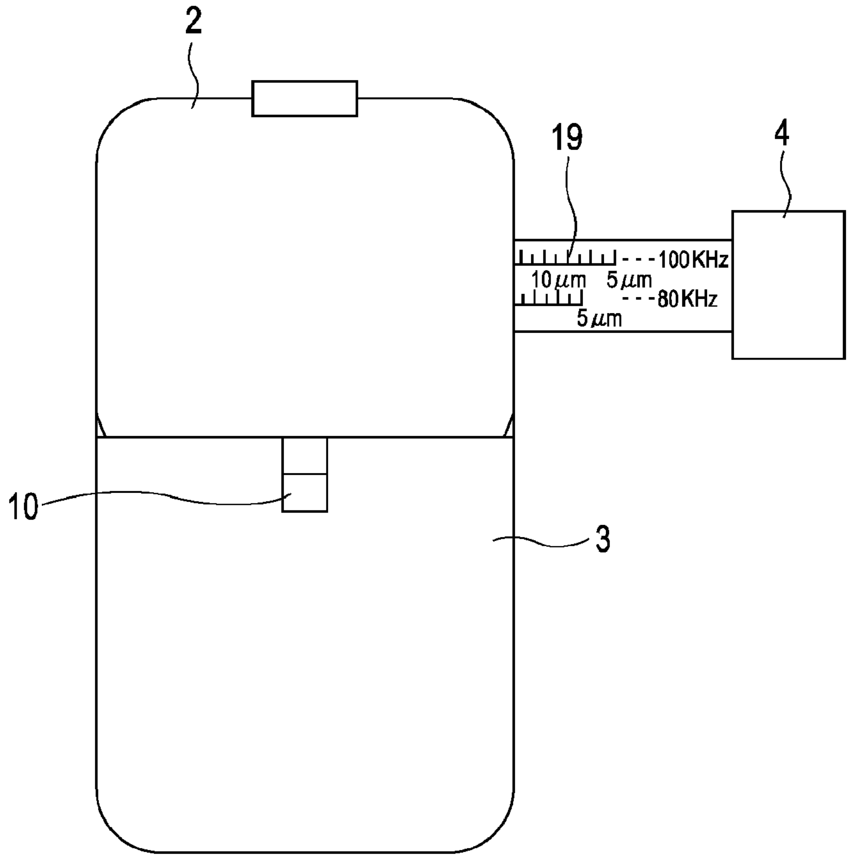
FIG. 7 is a plan view of a further modification of a passage-length changing unit.

Referring to FIG. 7, the relationship among the change amount of the passage length, the size of ejected droplets, and the ejection frequency is indicated as a scale (indicator) 19 on an outer surface of the air passage. For example, the relationship is indicated so that the user can recognize the change amount provided when the diameter of ejected droplets is 5 μm and the ejection frequency is 100 KHz. This allows the user to adjust the passage length to obtain an appropriate amount of evaporation, in accordance with the size and ejection frequency of the droplets.

A description will now be given of a passage-length determining unit that determines the distance from the opening 11 to the suction port 5*a* according to the use condition of the inhaler.

FIG. 8 is a table showing the relationship among the change amount of the passage length, the size of ejected droplets, and the ejection frequency. Numerical values in the table represent distances (passage lengths) needed to cause ejected droplets having different diameters (as listed across the top of FIG. 8) to change to have a diameter of 3 μm. The distances are calculated on the assumption that the air flow rate in the air passage is 10 m/s, the temperature is 25° C., and the outside humidity is 10%. As the size of ejected droplets increases, the humidity in the air passage easily increases. Therefore, the amount of evaporation is limited, and the distance (required passage length) increases. Further, as the ejection frequency increases, the number density (i.e., the density in terms of the number of droplets per unit volume) in the air passage increases and the humidity in the air passage easily increases. Therefore, the amount of evaporation is limited, and again the distance increases. The size of droplets can be adjusted by controlling the nozzle diameter of the head. In other words, while the term "size of ejected droplets" in this specification refers to the diameter of droplets immediately after they are ejected from the ejection head, it is directly tied to the nozzle diameter of the ejection head. Further, in this specification, the term "ejection frequency" refers to the number of pulse signals to be applied per unit time to the ejection energy generating element for ejecting medicine. In order constantly to obtain a proper amount of evaporation, a table is prepared to determine the change amount in accordance with the size of ejected droplets and the ejection frequency, as shown in FIG. 8. It is preferable that the inhaler according to the embodiment store this table in a CPU. The size of ejected droplets is determined in accordance with the ejection unit to be used. Accordingly, for example, when the user inputs the nozzle diameter of the head in the used ejection unit to the inhaler, reference to the table is made. For example, when the ejection unit is provided with a QR code indicating information about the nozzle diameter, it is preferable that the inhaler have a device for reading the QR code. Since the ejection frequency can be preset in the inhaler, the table can be referred to according to the preset value.

Second Embodiment

In general, when the user performs every inhalation operation in the same condition, the passage length can be determined in view of the ejection frequency and the diameter of ejected droplets, only, serving as parameters that are inherently determined by the medicine cartridge or the inhaler. However, the inhaler according to the present invention is portable, and there is no guarantee that the user will use the inhaler in the same environment every time. In other words, the temperature and humidity in the use environment may change for each inhalation operation. These parameters may affect the evaporation of droplets.

Accordingly, in a second embodiment, a table is prepared by adding the relationships among the change amount of the passage length, temperature, humidity, and the air flow velocity in the air passage to the table of the first embodiment (see FIG. 8). This allows more accurate control over the diameter of the ejected droplets.

Figure 9:
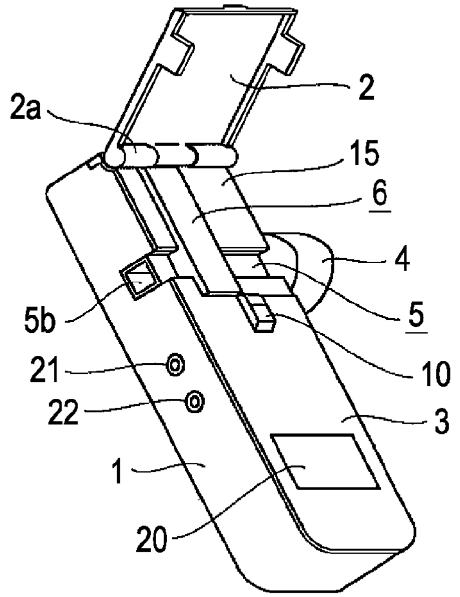
FIG. 9 is a perspective view showing a state in which an access cover of an inhaler according to a second embodiment is open.

FIG. 9 shows an inhaler including a hygrometer 21 and a thermometer 22 as a humidity measuring function and a temperature measuring function for obtaining information about the temperature and humidity. Measurement is performed simultaneously with power-on of the inhaler, and the measurement result is converted into electrical information and is displayed on a liquid crystal display unit 20 provided in the inhaler. As for the relationship between the passage length and temperature, since the saturation vapor pressure decreases and the amount of evaporation decreases as the temperature decreases, the passage length increases. As for the relationship between the passage length and humidity, since the amount of evaporation decreases as the humidity increases, the passage length increases. The user can adjust the length of the inhalation passage only with the functions provided in the inhaler, with reference to the table that shows the relationship among the change amount, temperature, and humidity, similarly to the relationship among the change amount, the size of droplets, and the ejection frequency shown in FIG. 8.

Figure 10:
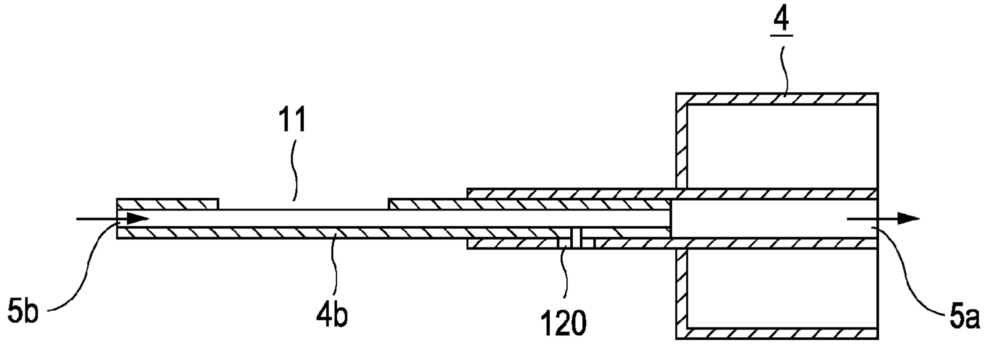
FIG. 10 is a schematic cross-sectional view of a modification of a passage-length changing unit in the second embodiment.

FIG. 10 shows a method in which a flow-velocity measuring function is added to an inhaler. A flow-velocity measuring function for obtaining information about the flow velocity in the air passage is realized by, for example, providing a pressure sensor 120 in the air passage. When the user starts inhalation and the pressure in the air passage changes, the pressure sensor 120 measures the pressure, and performs a calculation to obtain the flow velocity. The flow velocity is displayed on a liquid crystal display unit 20 serving as a display provided in the inhaler. Thus, the passage length can be adjusted only with the functions provided in the inhaler, with reference to the relationship between the change amount and the flow velocity found beforehand, similarly to the relationship among the change amount, the size of droplets, and the ejection frequency shown in FIG. 8. Instead of the pressure sensor, for example, a flowmeter can be used to measure the flow velocity.

Figure 11:
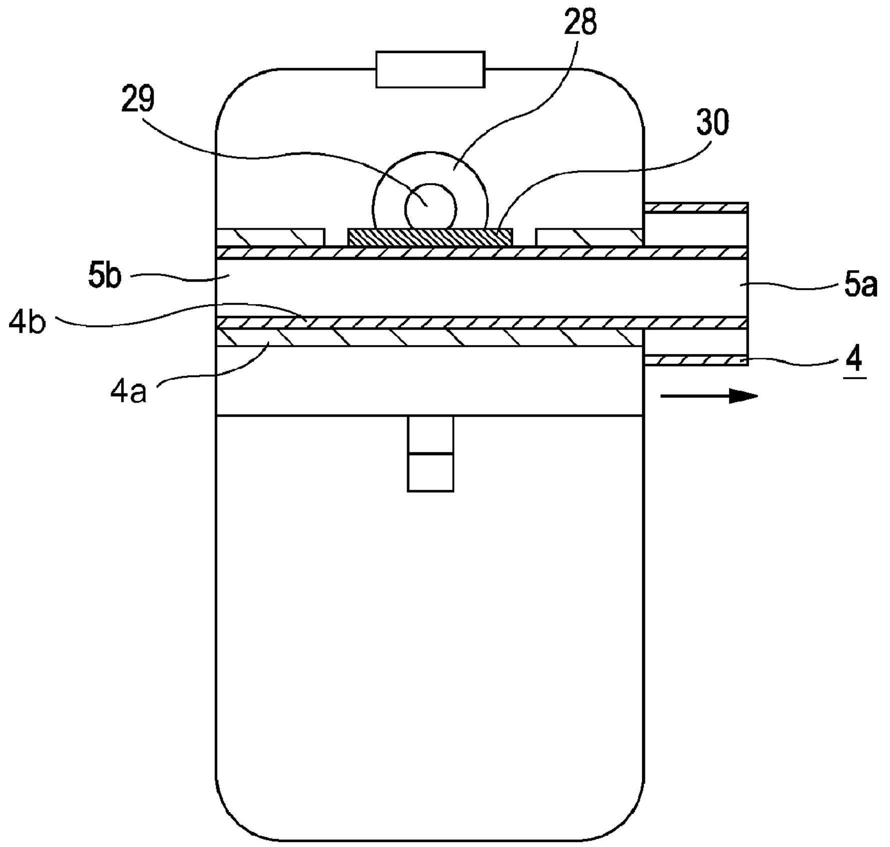
FIG. 11 is a schematic cross-sectional view of another modification of a passage-length changing unit.

Referring to FIG. 11, a linear driving mechanism for automatically adjusting the change amount of the passage length is added to the inhaler according to the second embodiment. A second passage forming member 4*b* is fitted in a first passage forming member 4*a* provided in a mouthpiece 4, and can slide relative to the first passage forming member 4*a*. A rack 30 is provided integrally with an outer surface of the second passage forming member 4*b*. By rotating a pinion 29 meshed with the rack 30 in forward and reverse directions by means of a motor 28, the second passage forming member 4*b* is moved in the direction of the arrow and in the opposite direction thereto. In other words, a rack-pinion mechanism is provided as a linear driving mechanism for automatically sliding the second passage forming member 4*b* relative to the first passage forming member 4*a*. This structure allows the passage length to be automatically adjusted to a value determined on the basis of the measurement results of the hygrometer 21 and the thermometer 22.

The rack-pinion mechanism in the second embodiment can be replaced with other linear driving mechanisms such as a fluid pressure cylinder or an electrical cylinder.

Figure 12:
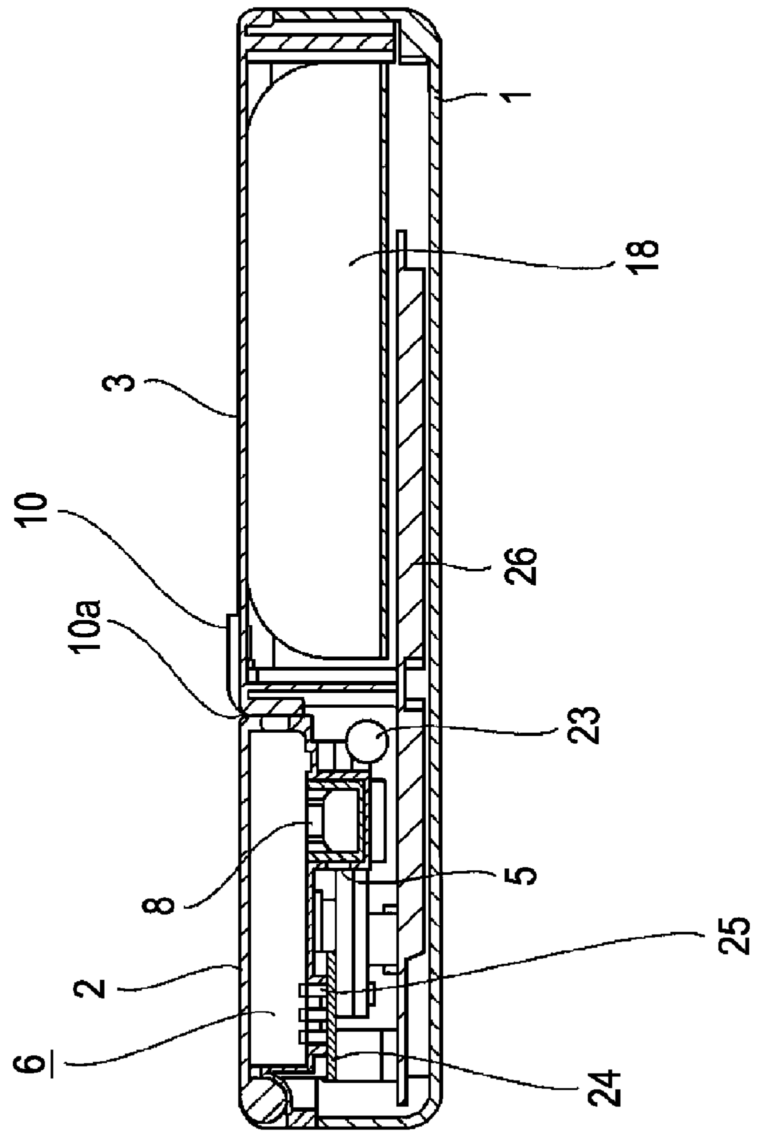
FIG. 12 is a schematic longitudinal sectional view of the entire inhaler.

FIG. 12 is a longitudinal cross-sectional view of the entire inhaler. The battery 18, a control substrate 26, and a probe substrate 24 electrically connected to the control substrate 26 via a cable or a connector are provided in the housing body 1. A contact probe 25 for supplying current to the electrical connection surface 9a of the medicine cartridge 6 is provided on the probe substrate 24.

A vibration motor 23 is provided in a space between the battery 18 and the mouthpiece 4 so as to be in contact with the control substrate 26. When inhalation is started and the flow rate of introduced air reaches a level that allows ejection, ejection of droplets is started. Simultaneously, the vibration motor 23 starts vibration so as to indicate the start of ejection. Since the pressure sensor 120 (see FIG. 13) provided in the air passage 5 detects a negative pressure produced in the air passage 5 by inhalation of the user, an inhalation profile of the user can be obtained. After ejection of a predetermined number of droplets is completed, the vibration motor 23 continues vibration for an auxiliary inhalation time so that an auxiliary amount of medicine is inhaled, on the basis of the inhalation speed calculated from the value measured by the pressure sensor 120, so that the last droplet reaches the lungs. This vibration promotes inhalation so that the medicine completely reaches the lungs. When the vibration of the vibration motor 23 stops, the patient stops inhalation.

Figure 13:
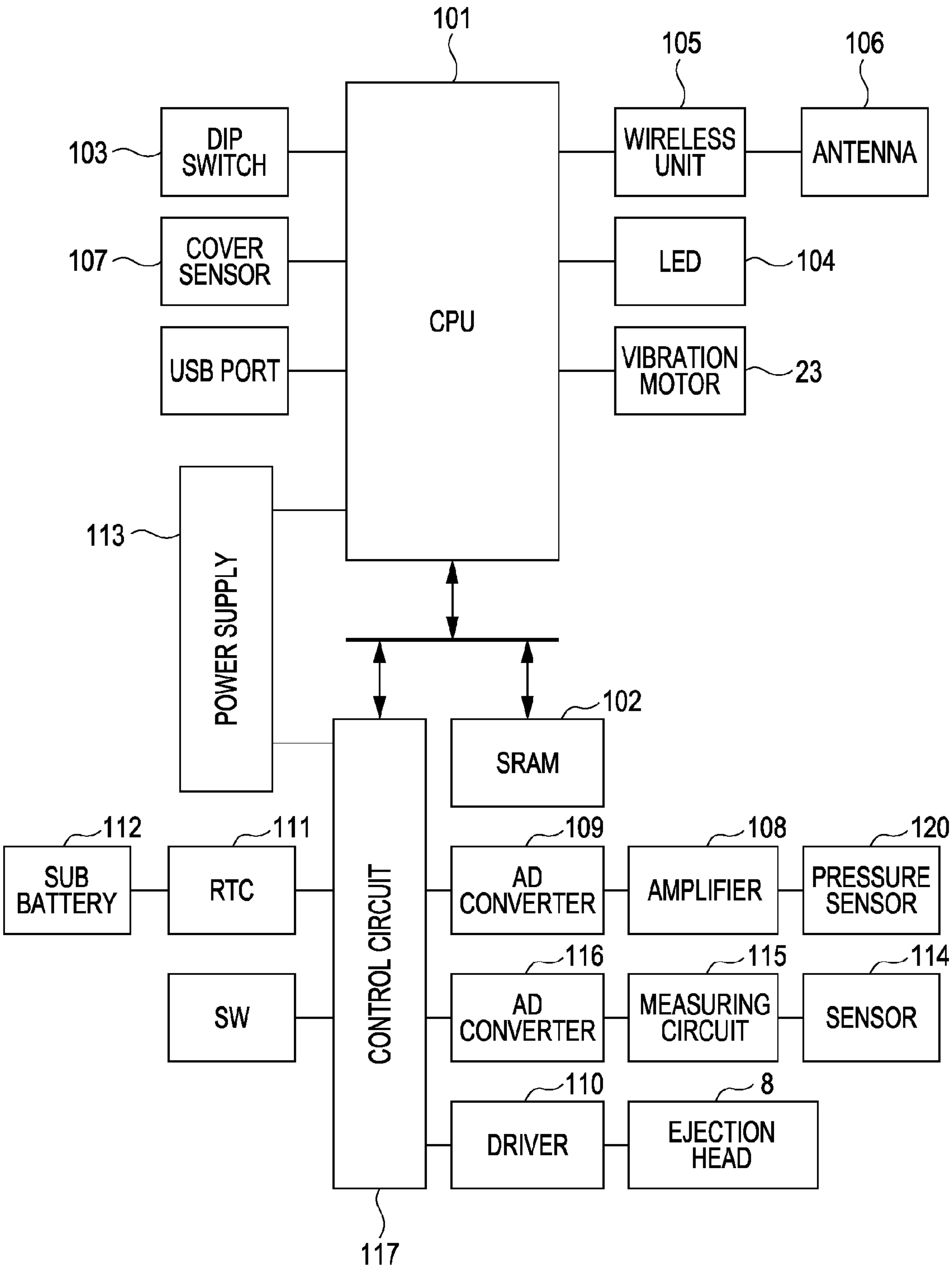
FIG. 13 is a block diagram of a control unit in the inhaler.

FIG. 13 is a block diagram of a control system in the inhaler. Referring to FIG. 13, the control system includes the following elements. A CPU 101 serves as an arithmetical processing unit, and incorporates a flash ROM that stores a program. When the program runs, an SRAM 102 serving as a read/write memory temporarily stores data. A DIP switch 103 is connected to a port of the CPU 101, and sets ON/OFF information and inputs the information to the CPU 101. An LED 104 serving as a display informs the user or maintenance operator of the state of the inhaler. A wireless unit 105 for wireless communication transfers the inhaler state and stored contents to a host and receives data from the host. An antenna 106 is provided for the wireless unit 105. A cover sensor 107 detects the open/closed state of the access cover 2. An amplifier 108 subjects the output from the pressure sensor 120 to level conversion and amplification. An AD converter 109 converts an analog output from the amplifier 108 into digital signals. A driver 110 controls the ejection head 8. A real-time clock ("RTC") 111 has a calendar function and a clock function. A sub-battery 112 backs up the RTC 111. A power supply 113 generates various voltages to be supplied to an electrical circuit, and includes a main battery, a charging circuit, a reset circuit, and a power switch. A sensor 114 detects the tilt of the inhaler. A measuring circuit 115 processes the output from the sensor 114. An AD converter 116 converts analog signals output from the measuring circuit 115 into digital signals. A control circuit 117 processes signals output from or input to various blocks, and is connected to the CPU 101 via a bus.

When a power switch is turned on, the power supply 113 outputs a reset signal to the CPU 101. In response to the reset signal, the CPU 101 is initialized, and starts operation according to the program stored in the internal flash ROM. The CPU 101 obtains a state of the DIP switch 103, and starts in a normal operation mode unless otherwise specially set. When the user performs inhalation, the output from the pressure sensor 120 changes, and the change is transmitted to the CPU 101 via the amplifier 108, the AD converter 109, and the control circuit 117. When the amount of inhalation exceeds a predetermined threshold value, the CPU 101 applies a voltage to the vibration motor 23 so as to start vibration. The CPU 101 also sends pulse signals to the ejection head 8 via the control circuit 117 and the driver 110. Thereby, medicine contained in the medicine cartridge 6 is ejected. After ejection is performed for a predetermined period, vibration continues for a predetermined period so as to urge the user to perform inhalation. Through these operations, the CPU 101 successively monitors tilt information from the sensor 114. When the tilt amount exceeds a first threshold value, the CPU 101 changes the amount of control over the ejection head 8 via the control circuit 117, so that the diameter of droplets ejected from the ejection head 8 is controlled. Further, when the tilt amount exceeds a second threshold value, the CPU 101 changes the vibration pattern of the vibration motor 23 so as to instruct the user not to tilt the inhaler further.

The present invention is not limited to the above embodiments and various changes and modifications can be made within the spirit and scope of the present invention. Therefore to apprise the public of the scope of the present invention, the following claims are made.

This application claims the benefit of Japanese Application No. 2007-281145 filed Oct. 30, 2007, which is hereby incorporated by reference herein in its entirety.

What is claimed is:

1. An inhaler configured to allow a user to inhale medicine from a suction port thereof, the inhaler comprising:
   an air passage through which the medicine passes, the air passage being connected to the suction port;
   an opening attached to a medicine ejection portion for ejecting the medicine, and provided in a part of the air passage so that the ejected medicine is released into the air passage through the opening;
   a passage-length determining portion configured to determine a proper distance from the opening to the suction port in accordance with a size of droplets of the medicine ejected from the medicine ejection portion and/or an ejection frequency; and
   a passage-length changing mechanism configured to change a distance from the opening to the suction port.

2. The inhaler according to claim 1, further comprising a first passage forming member, having the suction port, and a second passage forming member, having the opening, the first and second passage forming members being connected and together defining the air passage,
   wherein the passage-length changing mechanism allows sliding of the first passage forming member and the second passage forming member relative to each other.

3. The inhaler according to claim 2, wherein the passage-length changing mechanism includes a linear driving mechanism configured to cause sliding of the first passage forming member and the second passage forming member relative to each other in an axial direction.

4. The inhaler according to claim 1, further comprising:
   a display unit configured to display the distance from the opening to the suction port.

5. The inhaler according to claim 1, wherein the medicine ejection portion includes an electrothermal transducer configured to apply heat energy to the medicine.

6. The inhaler according to claim 1, wherein the passage-length changing mechanism automatically changes the distance based on the proper distance determined by the passage-length determining portion.

* * * * *